(12) United States Patent
Shelnutt et al.

(10) Patent No.: US 7,223,474 B1
(45) Date of Patent: May 29, 2007

(54) HETEROPORPHYRIN NANOTUBES AND COMPOSITES

(75) Inventors: John A. Shelnutt, Tijeras, NM (US); Craig J. Medforth, Winters, CA (US); Zhongchun Wang, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 11/440,484

(22) Filed: May 25, 2006

Related U.S. Application Data

(62) Division of application No. 11/001,468, filed on Dec. 1, 2004.

(51) Int. Cl.
*B32B 5/16* (2006.01)

(52) U.S. Cl. .................. 428/403; 977/744; 977/745

(58) Field of Classification Search .............. 428/403, 428/407; 977/744, 745
See application file for complete search history.

(56) References Cited

U.S. PATENT DOCUMENTS

| 6,733,828 | B2 * | 5/2004 | Chao et al. | 427/239 |
| 6,811,896 | B2 * | 11/2004 | Aziz et al. | 428/690 |
| 2003/0232982 | A1 | 12/2003 | Gong | |

OTHER PUBLICATIONS

Wang et al, "Self-Metallization of Photocatalytic Porphyrin Nanotubes", J. Am. chem. Soc. 2004, 126, 16720-16721.*
Nanotechnology News, "Tiny Porphyrin Tubes May Lead to New Nanodevices", www.azonano.com/news.asp?newsID=644, 2005.*
Snitka, Rackaitis, and Navickaite, "Self-Assembly of Porphyrin J-Aggregates", abstract, 2006 APS March Meeting.*
Crooks et al., "Dendrimer-Encapsulated Metal Nanoparticles: Synthesis, Characterizatioin, and Applications to Catalysis", Accounts of Chemical Research, vol. 34, No. 3, 2001, 181-190.*
Kim, Mayer, Zimmerman, A New Route to Organic Nanotubes from Porphyrin Dendrimers, Angew Chem Int Ed Eng, Mar. 10, 2003, 42(10), 1121-1126.*
Liu, "Metal-mediated coordination polymer nanotubes of 5,10,15,20-tetrapyridylporphine and tris(4-pyridyl)-1,3,5-triazine at the water-chloroform interface", Chem. commun., 2006, 3175-3177.*
Norberto Micali, Andrea Romeo, Rosaria Lauceri, Roberto Purello, Francesco Mallamace, and Luigi Monsu Scolaro, "Fractal Structures in Homo- and Heteroaggregated Water Soluble Porphyrins" J. Phys. Chem., B 2000, vol. 104. No. 40. pp. 9416-9420.
Ricardas Rotomskis, Ramunas Augulis and Vanentinas Snitka and Ramunas Valiokas and Bo Liedberg, "Hierarchical Structure of TPPS$_4$ J-Aggregates on Substrate Revealed by Atomic Force Microscopy", Am. Chem. Soc., 2004, vol. 108, No. 9 pp. 2833-2838.
Tatsuya Yamaguchi, Noriyuki Ishii, Kentaro Tashiro, and Takuzo Aida, "Supramolecular Peapods Composed of a Metalloporphyrin Nanotube and Fullerenes", J. Am. Chem. Soc., 2003, vol. 125, No. 46, pp. 13934-13935.
Jurgen-Hinrich Fuhrhop, Uwe Bindig, and Ulrich Siggel, "Micellar Rods and Vesicular Tubules Made of 14'", 16'" -Diaminoporphyrins", J. Am. Chem. Soc. 1993, vol. 115, No. 23, pp. 11036-11037.
Alexander D. Schwab, Deirdre E. Smith, Collin S. Rich, Elizabeth R. Young, Walter F. Smith, and Julio C. de Paula, "Porphyrin Nanorods," J. Phys. Chem. 2003, vol. 107, No. 41 pp. 11339-11345.
U. Siggel et al. "Photophysical and Photochemical Properties of Porphyrin Aggregates" Ber. Bunsenges. Phys. Chem 100, 1996, pp. 2070-2075.

* cited by examiner

*Primary Examiner*—H. Thi Le
(74) *Attorney, Agent, or Firm*—Carol I. Ashby

(57) ABSTRACT

Heteroporphyrin nanotubes, metal nanostructures, and metal/porphyrin-nanotube composite nanostructures formed using the nanotubes as photocatalysts and structural templates, and the methods for forming the nanotubes and composites.

17 Claims, 6 Drawing Sheets

HETEROPORPHYRIN NANOTUBES AND COMPOSITES

This application is a divisional application of the prior-filed copending U.S. nonprovisional patent application Ser. No. 11/001,468, filed on Dec. 1, 2004, and claims priority benefit therefrom. This prior-filed copending application is hereby incorporated by reference.

The United States Government has rights in this invention pursuant to Department of Energy Contract No. DE-AC04-94AL85000 with Sandia Corporation.

BACKGROUND OF THE INVENTION

This invention relates to heteroporphyrin nanostructures and composites thereof with incorporated metals. It is known that certain porphyrins in aqueous solution can form J-aggregates (off-set stacked molecules with aligned transition dipoles). The coherent coupling of the transition dipoles of porphyrin monomers gives rise to aggregate absorption bands that are significantly red-shifted relative to the monomer bands. Additional optical properties of the aggregates include giant resonance light scattering, which imparts intense color to a colloidal solution of such materials when viewed at an angle to the direction of propagation, and possible nonlinear optical properties.

These aggregates are typically in the form of fractal objects or nanoscale flecks of the aggregated porphyrin. An example of such fractal structures is reported in N. Micali et al., "Fractal Structures in Homo- and Heteroaggregated Water Soluble Porphyrins," J. Phys. Chem. B 104, 9416-9420 (2000).

The lack of linearity in the structure of these aggregates is a disadvantage for many possible applications of such materials where a well-defined morphology, such as nanotubes or nanorods, is desirable. This invention comprises a method for making nanotubular heteroporphyrin J-aggregates possessing a novel linear configuration and the nanotubes made thereby. The nanotubes comprise at least two types of porphyrin moieties with at least one positively charged porphyrin moiety and at least one negatively charged porphyrin moiety. It further comprises the nanostructures resulting from the metallization of these porphyrin nanotubes and the method of making them.

The formation of nanorods, fibers, tubules, helical ribbons, and sheets using a single porphyrin type as the molecular subunit has been previously reported, for example, by Furhop et al., "Micellar Rods and Vesicular Tubules Made of 14'", 16'"-Diaminoporphyrins," J. Am. Chem. Soc. 115 (1993) p. 11036-11037, Siggel et al., "Photophysical and Photochemical Properties of Porphyrin Aggregates," Ber. Bunsenges. Phys. Chem. 100 (1996) p. 2070-2075; Schwab et al., "Porphyrin Nanorods," J. Phys. Chem B 107 (2003) p. 11339-11345; and Rotomskis et al., "Hierarchical Structure of TPPS$_4$ J-Aggregates on Substrate Revealed by Atomic Force Microscopy," J. Phys. Chem. B 108 (2004) p. 2833-2383.

SUMMARY OF THE INVENTION

This invention comprises heteroporphyrin nanotubes and metal nanostructures and the method for making heteroporphyrin nanotubes and using the nanotubes for making the metal nanostructures and metal/porphyrin-nanotube composites.

Additional objects, advantages, and novel features of the invention will become apparent to those skilled in the art upon examination of the following description or may be learned by practice of the invention. The objects and advantages of the invention may be realized and attained as particularly pointed out in the appended claims.

BRIEF DESCRIPTION OF THE DRAWINGS

The accompanying drawings, which are incorporated in and form part of the specification, illustrate an embodiment of the present invention and, together with the description, serve to explain the principles of the invention.

DETAILED DESCRIPTION OF THE INVENTION

This invention comprises heteroporphyrin nanotubes, metal nanostructures, and metal/porphyrin-nanotube composite nanostructures formed using the nanotubes as photocatalysts and structural templates, and the methods for forming these structures.

Functional self-assembled materials with well-defined shapes and dimensions are of great current interest, especially for applications in electronics, photonics, light-energy conversion, and catalysis. In biological systems, tetrapyrroles such as porphyrins and chlorophylls are often organized into nanoscale biological superstructures that perform light-harvesting and energy- and electron-transfer functions. One example is the light-harvesting rods of the chlorosomes of green-sulfur bacteria, which are composed entirely of aggregated bacteriochlorophyll. Because of their desirable functional properties, porphyrins and other tetrapyrroles are attractive building blocks for functional nanostructures.

This invention comprises porphyrin nanotubes that can be prepared by ionic self-assembly of two oppositely charged porphyrins in aqueous solution. The charged porphyrins assemble by rapid ionic self-assembly to form multimolecular subunits. The multimolecular subunits then aggregate more slowly to form the nanotubes. The nanotubes of this invention represent a new class of porphyrin nanostructures whose structural and functional characteristics can be varied by proper selection of the molecular building blocks (tectons) used to form the nanostructure.

Figure 1:
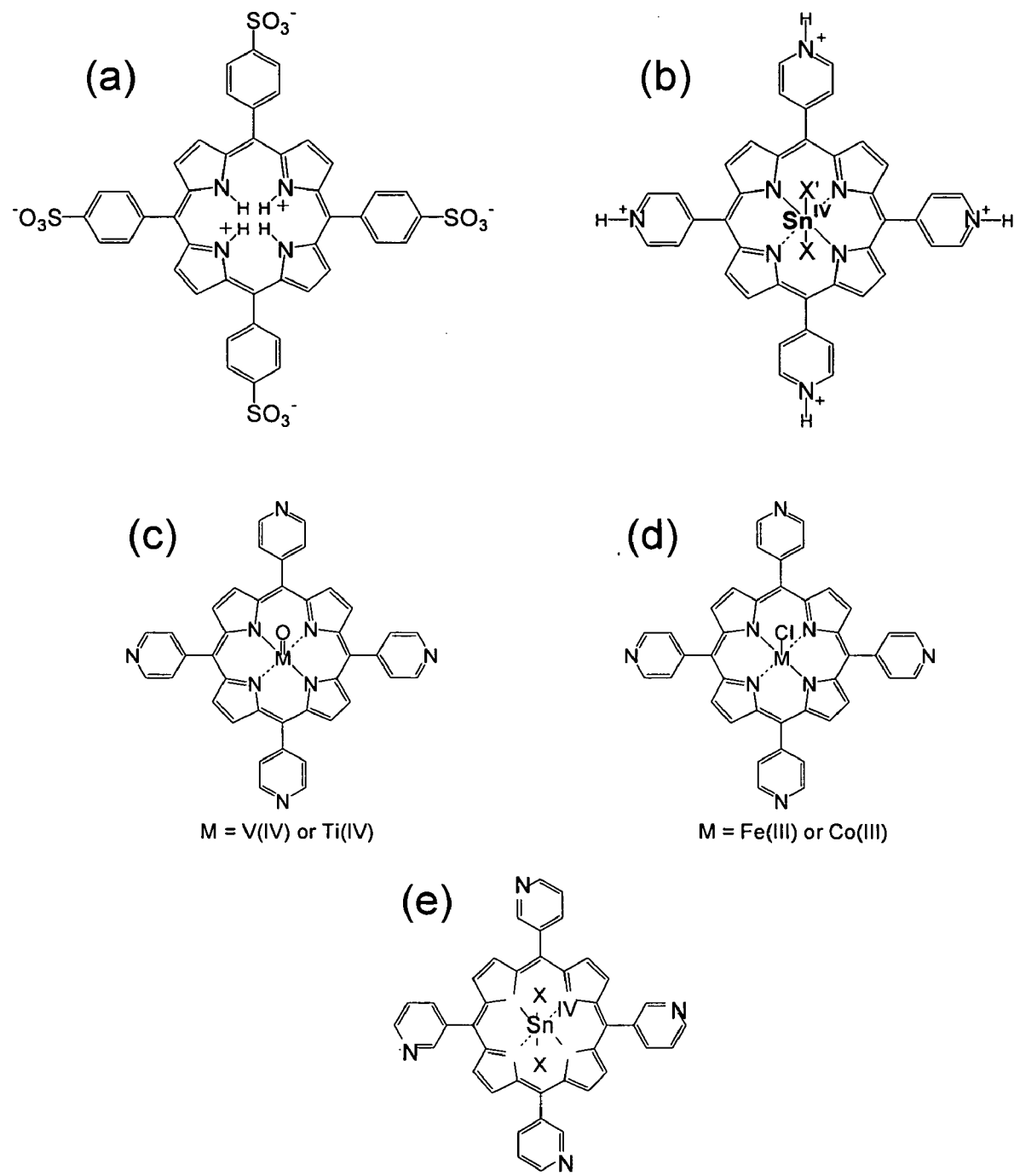
FIG. 1 illustrates the structure of some of the porphyrins and porphyrin precursors described herein: (a) meso-tetrakis(4-sulfonatophenyl)porphyrin, (b) Sn(IV)meso-tetrakis(4-pyridyl)porphyrin, (c) VO or TiO meso-tetrakis(4-pyridyl) porphyrin, (d) Fe(III) or Co(III)meso-tetrakis(4-pyridyl) porphyrin, and (e) Sn(IV)meso-tetrakis(3-pyridyl) porphyrin. In (b), (d), and (e), X and Cl represent a bound ligand such as, for example, halide, hydroxide, and water.

The porphyrin nanotubes are formed by ionic self-assembly of oppositely charged porphyrin molecules. Some examples of suitable porphyrins are shown in FIG. 1. The electrostatic forces between these porphyrin constituents promote the structural stability of these nanostructures. The multimolecular subunits formed from the combination of both positively and negatively charged porphyrins, including metalloporphyrins, provide the basic building blocks for the formation of the nanotube. Additional intermolecular interactions that can contribute to the structural stability include van der Waals forces, hydrogen bonding, axial coordination, and other weak intermolecular interactions. Molecular recognition of the complementary arrangements of the charges and H-bond donor/acceptors of the porphyrin guide the formation of the multimolecular subunits. The pH of the solution is important for providing the appropriate level of protonation of substituents of the porphyrins and of ligands bound to the metal ion in metalloporphyrins, such as, for example, hydroxyl groups, pyridyl groups, and bound water molecules. Formation of multimolecular subunits and their subsequent self-assembly into the nanotubes can be controlled by proper selection of the specific porphyrin constituents, the pH, and the solvent. Some examples of suitable metalloporphyrins include Co(III)meso-tetrakis(4-pyridyl)porphyrin, Fe(III)meso-tetrakis(4-pyridyl)porphyrin, Sb(IV)meso-tetrakis(4-pyridyl)porphyrin, Sn(IV)meso-tetrakis meso-tetrakis(4-pyridyl)porphyrin, TiO meso-tetrakis(4-pyridyl)porphyrin, VO meso-tetrakis(4-pyridyl)porphyrin, Co(III)meso-tetrakis(3-pyridyl)porphyrin, Fe(III)meso-tetrakis(3-pyridyl)porphyrin, Sb(IV)meso-tetrakis(3-pyridyl)porphyrin and Sn(IV)meso-tetrakis(3-pyridyl)porphyrin, TiO meso-tetrakis(3-pyridyl)porphyrin, and VO meso-tetrakis(3-pyridyl)porphyrin.

Figure 2:
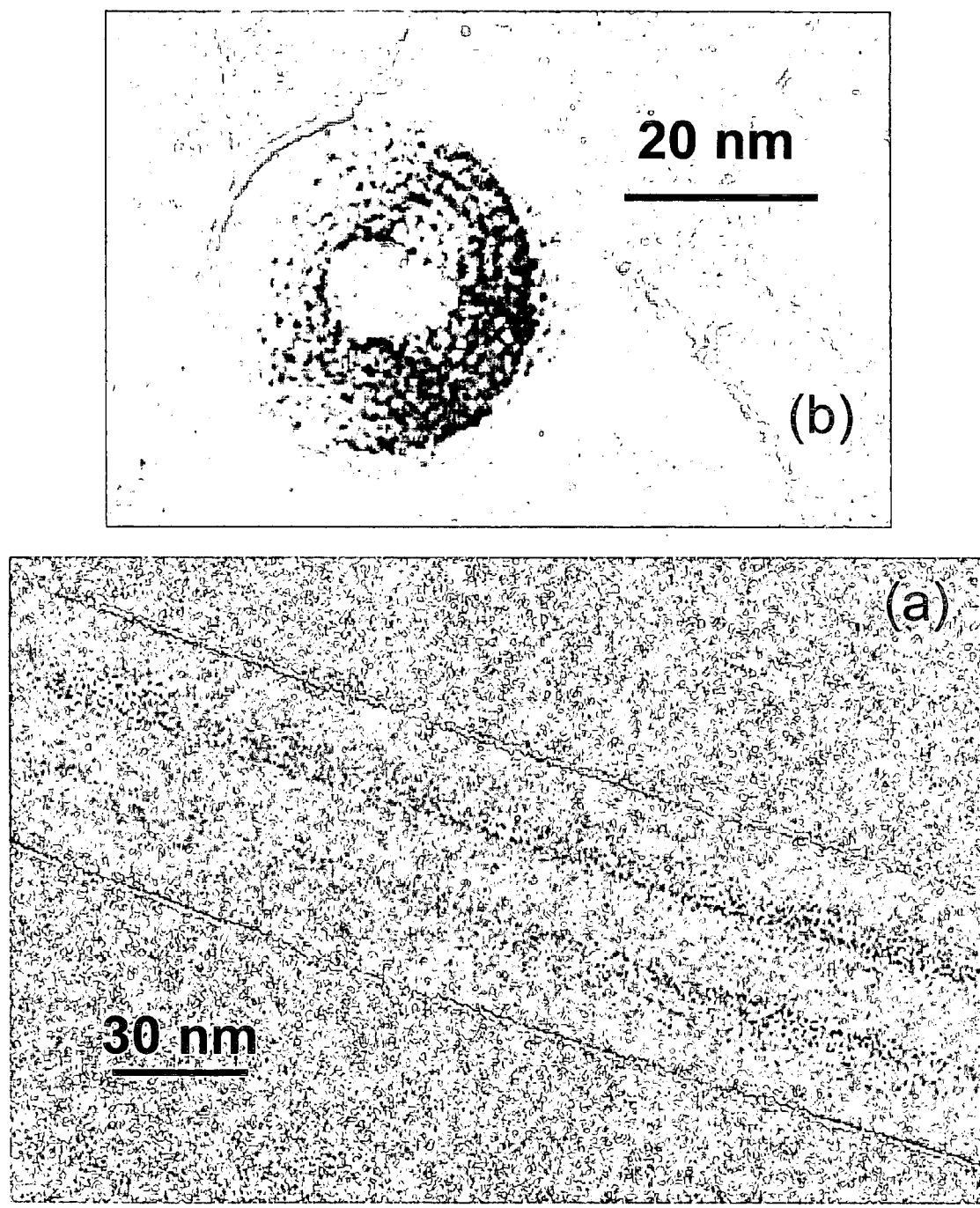
FIG. 2 consists of two transmission electron micrographs (TEMs) showing (a) a side view of a porphryin nanotube and (b) an end-on view of a porphyrin nanotube showing the hollow interior.
Figure 3:
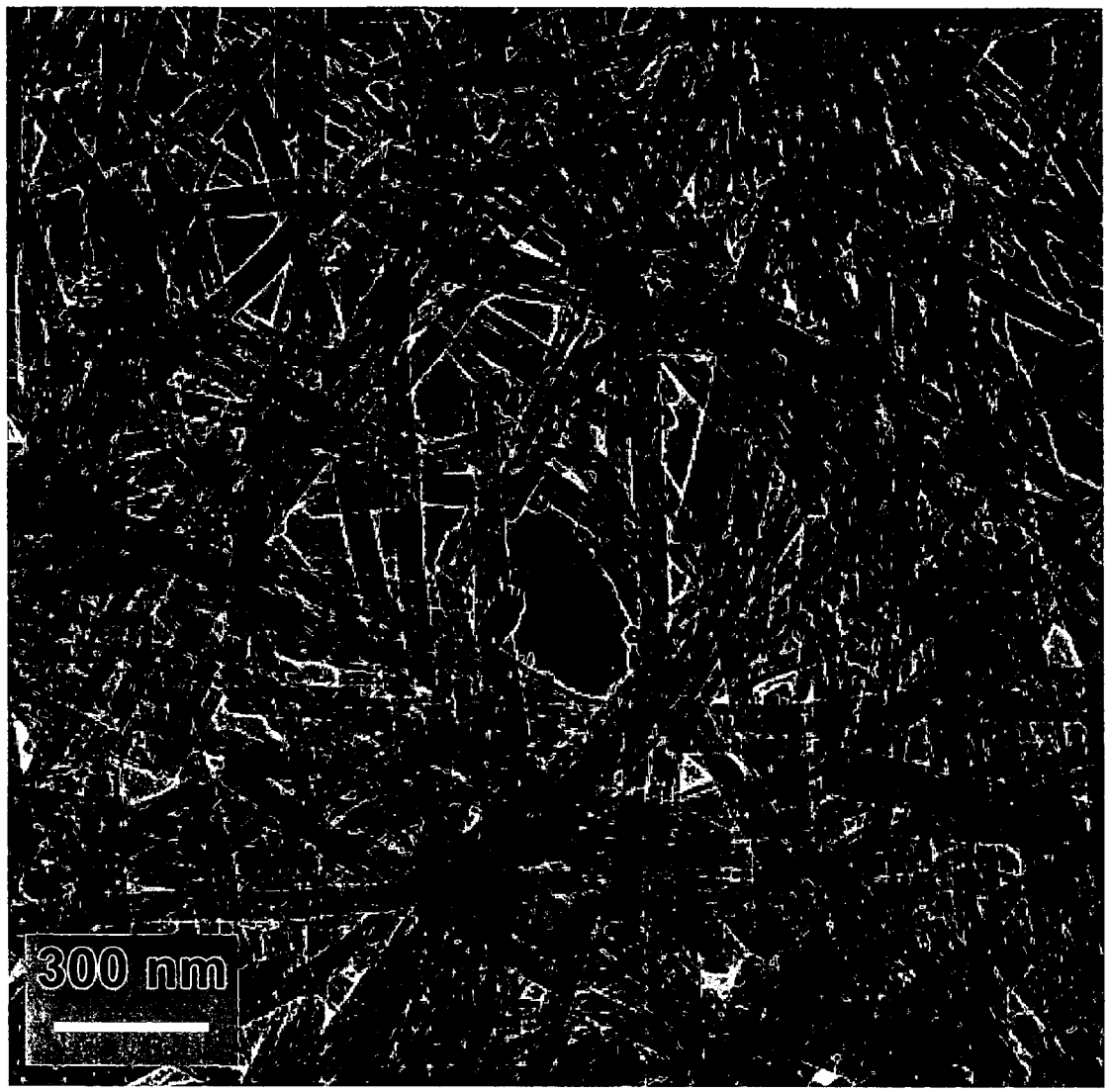
FIG. 3 is a TEM showing the uniformity of size and shape of the porphyrin nanotubes.

The porphyrin nanotubes of this invention are hollow structures possessing uniform size and shape for a given pair of cationic and anionic porphyrins, as shown in transmission electron micrographs (TEMs) in FIGS. 2 and 3. FIG. 2 shows the uniformity of wall thickness and the hollow interior of a single tube. FIG. 3 shows the high degree of uniformity of size for a large number of nanotubes generated in a single synthetic run. The nanotubes are photocatalytic, mechanically responsive and adaptive to light, and they have other interesting electronic and optical properties, some of which mimic properties of the chlorosomal nanorods.

In a typical embodiment, porphyrin nanotubes are formed by mixing aqueous solutions of the two or more porphyrin species with some porphyrin species being positively charged and others being negatively charged. The solvent of the aqueous solution can be water or its mixture with some other polar organic solvents, such as methanol, ethanol, acetonitrile, tetrahydrofuran, dimethyl formamide, and dimethyl sulfoxide.

In one embodiment, 9 mL of freshly acidified $H_4TPPS_4^{2-}$ solution (10.5 µM $H_4TPPS_4^{2-}$, 0.02 M HCl) was mixed with 9 mL of Sn(IV)tetrakis(4-pyridyl)porphyrin ($SnTPyP^{2+}$) dichloride in water (3.5 µM $SnTPyP^{2+}$). The mixture, which had a pH of 2, was left in the dark at room temperature for 72 h. While porphyrins of a single charge type exhibit negligible aggregation under these conditions (pH 2) within 5 hours, the mixture of both positively and negatively charged porphyrins immediately forms colloidal aggregates, which over a period of time self-organize into nanotubes with a high yield (approximately 90%). The nanotubes resulting from this synthetic process are illustrated in FIG. 2.

Transmission electron microscope (TEM) images of the porphyrin nanotubes (FIGS. 2 and 3) reveal that they are micrometers in length and have diameters in the range of 50-70 nm with approximately 20-nm thick walls. Images of the nanotubes caught in vertical orientations (FIG. 2(b)) confirm a hollow tubular structure with open ends. Fringes with 1.7-1.8-nm spacing are seen both in end-on views and at the edges of the nanotubes in TEM images and probably originate from the heavy tin and sulfur atoms in the porphyrin stacks. The fringes seen in the TEM images, combined with the optical spectral results discussed below, are consistent with a structure composed of stacks of offset J-aggregated porphyrins (individual porphyrins are approximately 2×2×0.5 nm) in the form of cylindrical lamellar sheets. The lamellar structure would be similar to an architecture proposed for the stacking of bacteriochlorophyll molecules in the chlorosomal rods. X-ray diffraction studies exhibit peaks in the low- and high-angle regions with peak widths suggesting moderate crystallinity.

The composition of the nanotubes was determined by UV-visible absorption spectroscopy and energy dispersive X-ray (EDX) spectroscopy. The filtered nanotubes were dissolved at pH 12 and the ratio of the porphyrins was determined by spectral simulation using extinction coefficients for $H_2TPPS_4^{4-}$ ($\epsilon_{552}$=5500 $M^{-1} \cdot cm^{-1}$) and $Sn(OH)_2TPyP$ ($\epsilon_{551}$=20200 $M^{-1} \cdot cm^{-1}$), giving an approximate molar ratio of 2.4 $H_4TPPS_4^{4-}$ per $Sn(OH)_2TPyP$. EDX measurements of the S:Sn atomic ratio of the porphyrin tubes on the TEM grids also indicate a molar ratio of between 2.0 and 2.5. The observed ratio of the two porphyrins in the tubes (2.0-2.5) can be related to the charges of the porphyrin species present at pH 2. As shown by titrations monitored by UV-visible spectroscopy, the porphyrin species present at pH 2 are $H_4TPPS_4^{2-}$ and a mixture of $Sn(OH)_2TPyP^{4+}$ and $Sn(OH)(H_2O)TPyP^{5+}$ (formed by protonation of the pyridine substituents of $Sn(OH)_2TPyP$ and, in the latter species, by the additional replacement of one $OH^-$ axial ligand with $H_2O$ at low pH). The formation of the nanotubes critically depends on the pH (e.g., not formed at pH 1 or 3), as expected because the charge balance of the ionic porphyrins depends on their protonation state. EDX spectra of the nanotubes also showed no evidence of significant amounts of Cl (or I when HI was used in place of HCl), precluding the presence of chloride as counter ions, axial ligands, or salt bridges. As expected for a nanostructure formed by ionic self-assembly, the same ratio of porphyrins (2.0-2.5) is observed in the nanotubes regardless of the initial ratio of the two porphyrins in solution.

By altering the molecular structure of the porphyrins, the dimensions of the nanotubes can be controlled. For example, by using Sn tetra(3-pyridyl)porphyrin instead of Sn tetra(4-pyridyl)porphyrin, nanotubes with significantly smaller average diameters were obtained (35 nm instead of 60 nm). Changing the tin porphyrins subtly repositions the charge centers and the associated H-bond donor atoms on the pyridinium rings, changing the inter-porphyrin interactions sufficiently to alter the diameter while still allowing the tubes to form. Nanotubes are not produced when the 2-pyridyl porphyrin is used, presumably because the location of the functional nitrogen atom is changed too drastically. Axial ligation of a porphyrin is also important as tubes are obtained when the Sn(IV) complex is replaced with other potentially six-coordinate metal ions, for example, $Fe^{3+}$, $Co^{3+}$, $TiO^{2+}$, $VO^{2+}$, but not when a metal that does not add axial ligands, for example, $Cu^{2+}$, or the metal-free porphyrin is used. These results illustrate the possibility of achieving a control over the structure of the nanotubes by suitable structural modifications of the porphyrins, including variation of the peripheral substituents of the porphyrin, the metal contained in the porphyrin core, and the nature of the axial ligands.

The nanotubes exhibit interesting and potentially useful properties. For example, the porphyrins in the nanotubes are stacked in a manner that gives UV-visible absorption bands at 496 and 714 nm that are red-shifted from the corresponding bands of the monomeric porphyrins. These bands indicate formation of J-aggregates similar to those of $H_4TPPS_4^{2-}$ and other porphyrins, but the bands of the nanotubes are broader. As a result, the nanotubes exhibit intense resonant light scattering from these J-aggregate bands, making the nanotube suspension appear bright green under intense white light illumination, but light greenish yellow in weak transmitted light. In addition, the strong fluorescence of the porphyrin monomers is almost entirely quenched in the nanotubes.

A potentially useful property of the nanotubes is their ability to respond mechanically to light illumination. Even though they are stable for months when stored in the dark, irradiation of a suspension of the tubes for just five minutes using incandescent light from a projector lamp (800 nmol-$cm^{-2} \cdot s^{-1}$) results in TEM images showing rod-like structures instead of tubes. This response to light is reversible, as the tubes reform (self-heal) when left in the dark. The switch from tubular to rod-like structures in the TEM images suggests a softening of the tube walls and a collapse of the tube structure, perhaps as a result of photoinitiated intermolecular electron transfer that disrupts the charge balance and hence the rigidity of the structure of the ionic solid.

Some metalloporphyrins, for example, the Sn(IV) porphyrins, are known to be good photocatalysts in homogeneous solutions. Porphyrin nanotubes with constituent tin porphyrins exhibit useful photocatalytic activity. This has been demonstrated in two embodiments of this invention where the photoreduction of aqueous metal complexes has been used to form metal nanostructures using the porphyrin nanotubes as structural templates. The two types of metal salts employed to demonstrate this invention in these two embodiments are Au(I) complexes and Pt(II) complexes. The photocatalytic reduction reaction mediated by Sn(IV) porphyrins in homogeneous solutions is described for reduction of a Au(I) complex by the following simplified cyclic reactions:

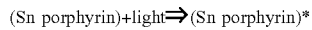

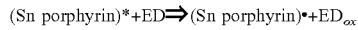

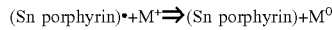

where ED=electron donor, * indicates a photoexcited state of the porphyrin, • indicates the reduced porphyrin or porphyrin radical ion, $ED_{ox}$ is the oxidized form of the electron donor, and $M^+$ and $M^0$ indicate the metal ion and reduced metal, respectively. Typical examples of electron donors include but are not restricted to ascorbic acid, ethylene diamine tetra-acetic acid (EDTA) in varying degrees of protonation, triethylamine, triethanolamine, benzenethiol, 2-mercaptoethanol, and nitrite ions.

In one embodiment, Au(I) thiourea or Au(I) thiosulfate complexes were used with ascorbic acid as the electron donor (ED). These reductions are predominately photocatalytic, unlike those for many other gold complexes that may also involve chemical and photochemical reduction. The photochemical reduction is prevented by the higher stability of the Au(I) complexes relative to Au(III) complexes and their transparency to visible light. Autocatalytic growth of gold is negligible.

Figure 4:
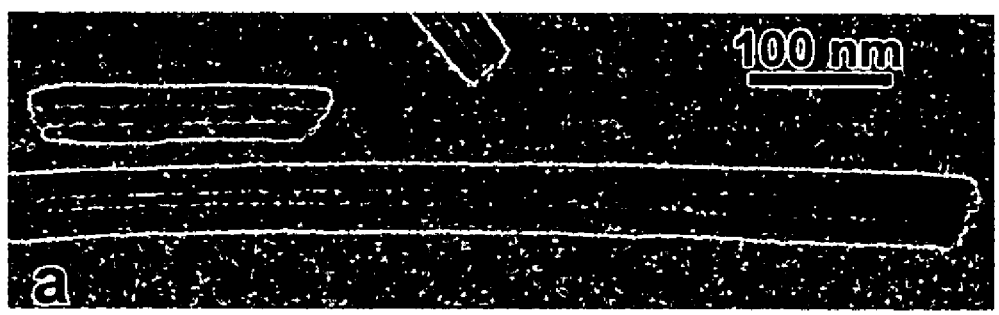
FIG. 4 consists of three TEMs showing (a) a porphyrin nanotube, (b) a gold metal nanostructure consisting of a nanorod and a continuously attached nanoball that has been grown using the nanotube as a structural template, and (c) a gold nanorod with a continuously attached nanoball (a ball-and-rod nanostructure) from which the porphyrin template has been removed by treatment with NaOH at pH 10.
Figure 4:
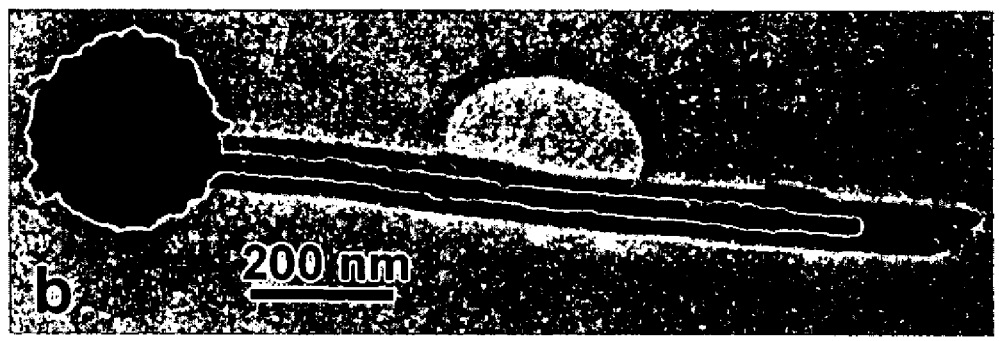
Figure 4:
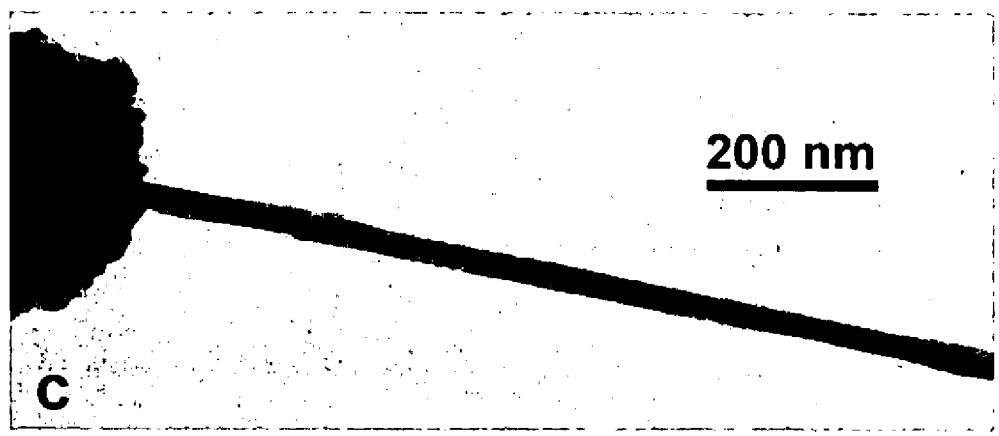

The Sn-porphyrin-containing nanotubes used in the metallization reactions were prepared as described above. A transmission electron microscope (TEM) image of the porphyrin nanotubes before metal deposition is shown in FIG. 4(a). The tubes can be several micrometers in length and have diameters typically in the range of 50-70 nm with approximately 20-nm thick walls. When the nanotubes are used to photoreduce the positively charged Au(I)-thiourea complex, the metal is deposited exclusively within the hollow interior of the nanotubes, forming a continuous polycrystalline gold nanowire that is of the same diameter as the tube core, as shown in FIG. 4(b). The nanowires can be terminated at one end of the nanotube with a gold ball that is generally of larger diameter than the tube. When the porphyrin nanotubes are dissolved by raising the pH, the gold wire and ball remain intact as shown in FIG. 4(c). The diameter of the nanorod is determined by the inner diameter of the hollow porphyrin nanotube. The diameter of the ball can vary from about the same diameter as the nanotube to much larger. Nanoball diameters up to 800 nm have been demonstrated and larger-diameter nanoballs are possible, depending on the reaction conditions and growth time after the nanogrowth emerges from the interior of the nanotube.

Selection of a negatively charged gold complex can produce a different nanostructure. In one embodiment, the reduction of the negatively charged Au(I) thiosulfate complex produces gold particles primarily on the outer surfaces of the tubes. These results show that the electrostatic and other interactions between the complex and the tube surfaces can control where the metal is deposited and the location of the metal deposition is different for the two oppositely charged complexes. Directional electron/energy transport within the tube walls can also play a role in determining where the metal is deposited.

In one embodiment, gold solutions for the photocatalytic deposition of gold were freshly prepared by reducing Au(III) to Au(I) with thiourea (V. Gaspar, A. S. Mejerovich, M. A. Meretukov, and J. Schmiedl, *Hydrometallurgy*, 1994, 34, 369). Typically, 17 mg of thiourea powder was slowly added to 1 ml of $HAuCl_4$ solution (20 mM) and the mixture agitated to dissolve the thiourea. After a few minutes, the yellow Au(III) solution turned into a transparent and colorless solution of $Au(I)(thiourea)_x$ complex. To grow the Au nanostructure, 50 µl of $Au(I)(thiourea)_x$ solution (20 mM Au) and 50 µl of ascorbic acid solution (0.2 M) were added to a 2-ml glass vial containing 1 ml of the nanotube colloidal suspension ($SnTPyP^{2+}$ concentration 1.75 µM). The reaction mixture was swirled to homogenize the solution, placed in a glass water bath to control the temperature, and then irradiated with incandescent light (800 nmol $cm^{-2}$ $s^{-1}$) for 8 minutes. No gold deposition was observed in control experiments without light exposure or in the absence of the porphyrin nanotubes.

The continuous nature of the nanowire and the formation of the ball at the end of the tube suggest a novel mechanism for its formation by the nanotube. The continuity of the wire implies a single nucleation site on the inner surface with mobile electrons generated in the tube flowing into the wire at that site. Thus, under illumination, the tube acts as a photoelectrochemical cell, charging up the growing nanowire at a potential negative enough to reduce the gold complex at gold surfaces accessible to the complex. When the wire reaches the end of the tube it expands into the ball where most of the electrons will collect. The J-aggregate composition of the tube walls indicates strong electronic coupling of multiple porphyrin subunits, which might be expected to facilitate electron transport necessary to grow the nanowire.

Figure 5:
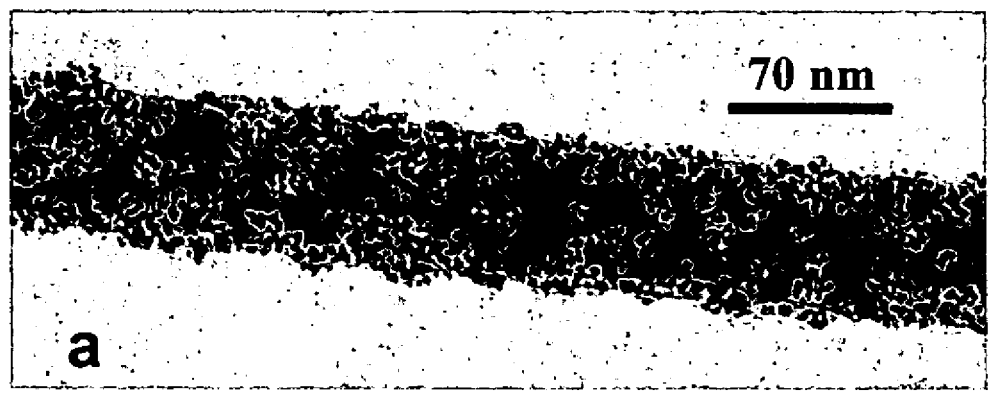
FIG. 5 consists of TEMs showing metallic platinum nanostructures where the platinum has been deposited (a) on the surface of a porphyrin nanotube, (b) within the hollow interior of the porphyrin nanotube, and (c) both within the hollow interior of the porphyrin nanotube and on the outer surface of the porphyrin nanotube.
Figure 5:
Figure 5:
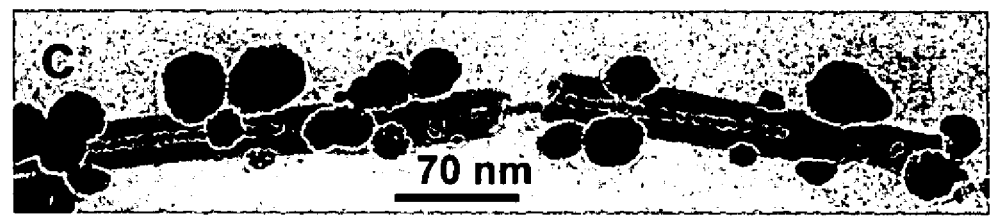

In one embodiment of platinum nanostructures formed in this invention, platinum metal can be grown onto the nanotube surfaces as illustrated in FIG. 5(a). Photocatalytic initiation of growth by photoreduction of the platinum complex occurs with the nanotubes to produce small Pt seed nanoparticles. These seed particles decorate mainly the outer surfaces of the porphyrin nanotubes, as shown in FIG. 5(a). Normally, fast autocatalytic reduction of Pt occurs after the seed particle reaches a certain size, producing a Pt dendrite, and some nascent Pt dendrites are visible in high magnification TEM images. At higher Pt concentrations, it is possible to grow one or more Pt dendrites or columns of Pt nanoparticles within the hollow interior of the nanotube, as shown in FIG. 5(b). FIG. 5(c) shows Pt nanostructures both within the hollow interior and on the outer surface of the nanotube. The concentrations of the Pt complex and ascorbic acid were 0.1 and 1 mM, respectively, for (a) and 1 and 10 mM, respectively, for (b) and (c). Exposure times were 15 minutes for (a) and (b) and 35 minutes for (c). The concentrations of the nanotubes were the same for both reactions. Composites with both filled cores and large platinum dendrites on the outer surface can also be produced at high Pt ion concentration and longer light exposure times.

In one embodiment for the deposition of platinum, $K_2PtCl_4$ stock solution (20 mM Pt) and ascorbic acid stock solution (0.2 M) were added to a 2-ml glass vial containing 1 ml of the nanotube colloidal suspension ($SnTPyP^{2+}$ concentration 1.75 µM). The reaction mixture was swirled to homogenize the solution, placed in a glass water bath to control the temperature, and then irradiated with incandescent light (800 nmol $cm^{-2}$ $s^{-1}$). When a low concentration of platinum salt (0.1 mM) was used in the reaction, 5 µl of $K_2PtCl_4$ stock solution and 5 µl of ascorbic acid stock solution were added and the light exposure time was 15 min. When a high concentration of platinum salt (1 mM) was employed in the reaction, 50 µl of $K_2PtCl_4$ stock solution and 50 µl of ascorbic acid stock solution were added and the light exposure time was 15 or 35 min. The porphyrin concentration was essentially the same for all the reactions (1.75 µM $SnTPyP^{2+}$).

It is possible to construct metallic nanostructures that comprise one metal within the nanotube and different metal on the outer surface of the nanotube. In one embodiment, a Pt core is formed within the nanotube and dendritic Au is grown on the surface of the nanotube. This was accomplished by growing the Pt as follows: 100 µl $K_2PTCl_4$ solution (20 mM inPt) and 100 µl of 0.2 M ascorbic acid solution were added to a 2-ml glass vial containing 1 ml of the nanotube colloidal suspension ($SnTPyP^{2+}$ concentration 1.75 µM). The reaction mixture was mixed to homogenize the solution, placed in a water bath to control the temperature, and irradiated with incandescent light (800 nmol $cm^{-2}$ $s^{-1}$) for 11 min. The suspension was centrifuged at 2000 rpm for 2 minutes. The supernatant liquid was removed and 1 ml of 0.01 M HCl was added. Following mixing to obtain a relatively homogeneous suspension, 100 µl of 0.2M ascorbic acid solution and 100 µl of 20 mM Au(I) thiourea$_x$ complex were added. The reaction mixture was mixed to homogenize the solution, placed in a water bath to control the temperature, and irradiated with incandescent light (800 nm $cm^{-2}$ $s^{-1}$) for 9 minutes. The structure resulting from such growth procedures is shown in FIG. 6(a).

Figure 6:
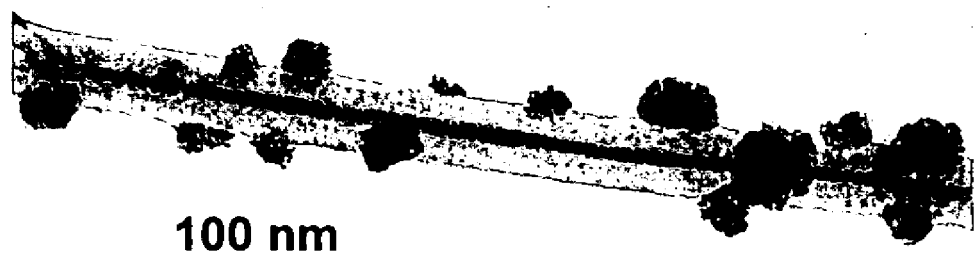
FIG. 6 consists of TEMs showing metallic nanostructures where metal deposited within the hollow interior of the porphyrin nanotube differs from the metal deposited on the surface of the nanotube. (a) Pt within a porphyrin nanotube and Au on the surface of the porphyrin nanotube. (a) Au within a porphyrin nanotube and Pt on the surface of the porphyrin nanotube.
Figure 6:
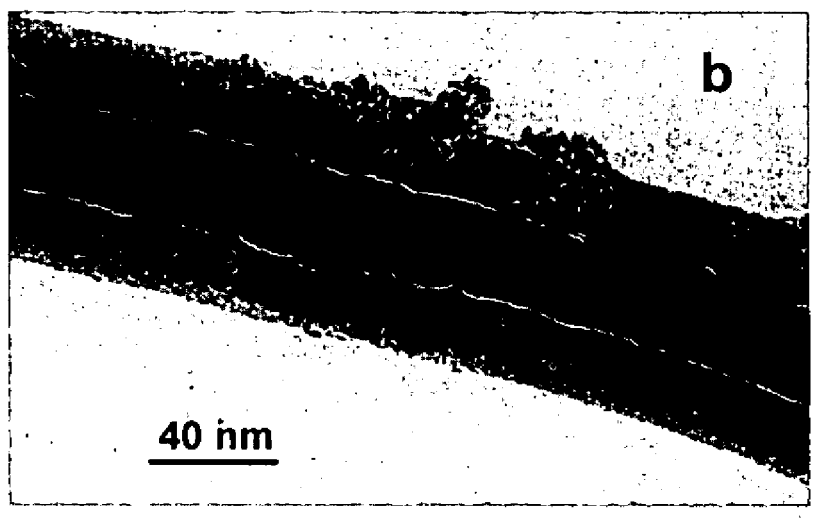

Composite structures with Au interior wires and Pt nanoparticles on the outer surface of the nanotube can be made, as shown in FIG. 6(b). In one such embodiment, 50 µl of 20 mM Au(I) thiourea$_x$ complex and 100 µl of 0.2 M ascorbic acid were added to a 2-ml glass vial containing 1 ml of the nanotube colloidal suspension ($SnTPyP^{2+}$ concentration 1.75 µM). The reaction mixture was mixed to homogenize the solution, placed in a water bath to control the temperature, and irradiated with incandescent light (800 nmol $cm^{-2}$ $s^{-1}$) for 6 min. The suspension was centrifuged at 1500 rpm for 1 min. The supernatant liquid was removed. One milliliter of Pt nanoparticle colloidal suspension prepared according to the literature (Brugger, P. A.; Cuendet, P.; Gratzel, M. *J. Am. Chem. Soc.* 1981, 103, 2923-2927) and 10 µl of 1 N HCl were added; the resulting suspension was mixed to achieve relative homogeneity The mixed suspension was kept in the dark overnight while the Pt nanoparticles reacted and adsorbed onto or bound to the porphyrin nanotube outer surface.

The preceding embodiments illustrate this invention using Au(I) and Pt(II) ions. This invention is applicable to a range of other metal that have reduction potentials compatible with the potential provided by the photoreduced metalloporphyrin incorporated within the nanotube. Examples include but are not restricted to Ag(I) ions, Pd ions, Ni ions, Cu ions, Co ions, Fe ions, Rh ions, Pb ions, oxides of Ru, Cr, and U, and Se(IV), for example, as in $SeO_3^{2-}$.

It should be apparent that there are many modifications possible with this invention. It is intended that the scope of the invention be defined by the appended claims.

What is claimed is:

1. A metal nanostructure, comprising:
    a porphyrin nanotube with a hollow interior, the porphyrin nanotube having an outer surface; and
    a metal nanorod within the hollow interior, the metal nanorod having a first end and a second end.

2. The metal nanostructure of claim 1, further comprising a metal ball attached to the first end of the metal nanorod.

3. The metal nanostructure of claim 1, further comprising a metal film on the outer surface of the porphyrin nanotube.

4. The metal nanostructure of claim 1, further comprising a metal particle on the outer surface of the porphyrin nanotube.

5. The metal nanostructure of claim 1, wherein the porphyrin nanotube comprises a metalloporphyrin with a coordinated metal ion.

6. The metal nanostructure of claim 5, wherein the coordinated metal ion is selected from the group consisting of antimony, cobalt, iron, tin, titanium, and vanadium.

7. The metal nanostructure of claim 5, wherein the metalloporphyrin is selected from the group consisting of Co(III)meso-tetrakis(4-pyridyl)porphyrin, Fe(III)meso-tetrakis(4-pyridyl)porphyrin, Sb(IV)meso-tetrakis(4-pyridyl)porphyrin, Sn(IV)meso-tetrakis meso-tetrakis(4-pyridyl)porphyrin, TiO meso-tetrakis(4-pyridyl)porphyrin, VO meso-tetrakis(4-pyridyl)porphyrin, Co(III)meso-tetrakis(3-pyridyl)porphyrin, Fe(III)meso-tetrakis(3-pyridyl)porphyrin, Sb(IV)meso-tetrakis(3-pyridyl)porphyrin and Sn(IV) meso-tetrakis(3-pyridyl)porphyrin, TiO meso-tetrakis(3-pyridyl)porphyrin, and VO meso-tetrakis(3-pyridyl)porphyrin.

8. The metal nanostructure of claim 1, wherein the porphyrin nanotube comprises J-aggregated porphyrins.

9. The metal nanostructure of claim 1, wherein the metal nanostructure comprises at least one material selected from the group consisting of Au, Pt, Pd, Ag, Fe, Co, Ni, Cu, Rh, Pb, Se, $CrO_2$, $RuO_2$, and $UO_2$.

10. A metal nanostructure, comprising:
a porphyrin nanotube with a hollow interior, the porphyrin nanotube having an outer surface;
a first metal nanorod within the hollow interior, the first metal nanorod having a first end and a second end; and
a second metal deposit on the outer surface.

11. The metal nanostructure of claim 10, further comprising a metal ball attached to the first end of the first metal nanorod.

12. The metal nanostructure of claim 10, wherein the first metal nanorod and the second metal deposit comprise at least one material selected from the group consisting of Au, Pt, Pd, Ag, Fe, Co, Ni, Cu, Rh, Pb, Se, $CrO_2$, $CrO_3$, $RuO_2$, and $UO_2$.

13. The metal nanostructure of claim 10, wherein the first metal nanorod and the second metal deposit contain at least one different metallic element.

14. The metal nanostructure of claim 10, wherein the porphyrin nanotube comprises a metalloporphyrin with a coordinated metal ion.

15. The metal nanostructure of claim 14, wherein the coordinated metal ion is selected from the group consisting of antimony, cobalt, iron, tin, titanium, and vanadium.

16. A metal nanostructure comprising a ball-and-rod nanostructure, made by a method comprising:
preparing a solution of a porphyrin nanotube, a metal precursor, and an electron donor, the porphyrin nanotube having a hollow interior, a first end, and a second end;
illuminating the solution with a light beam at a wavelength that produces a photoexcitation of the porphyrin nanotube, thereby making a photoexcited porphyrin-nanotube template;
photoreducing the metal precursor by means of the photoexcited porphyrin-nanotube template to form a metal nanorod inside the hollow interior of the porphyrin nanotube,
photoreducing the metal precursor by means of the photoexcited porphyrin-nanotube template to form a metal ball continuously attached to the metal nanorod at the first end of the porphyrin nanotube to form the ball-and-rod nanostructure; and
removing the porphyrin nanotube from the ball-and-rod nanostructure using a basic solution.

17. The metal nanostructure of claim 16, wherein a diameter of the metal nanorod is between about 5 nm and about 200 nm and a diameter of the metal ball is between the diameter of the metal nanorod and 1 micrometer.

* * * * *